United States Patent
Thornton

(10) Patent No.: US 9,901,279 B2
(45) Date of Patent: Feb. 27, 2018

(54) QEEG CORRELATES OF EFFECTIVE COGNITIVE FUNCTIONING—MEMORY AND PROBLEM SOLVING—IN DIVERSE CLINICAL CONDITIONS AND NORMAL POPULATIONS

(71) Applicant: Kirtley Elliott Thornton, Clover, SC (US)

(72) Inventor: Kirtley Elliott Thornton, Clover, SC (US)

( * ) Notice: Subject to any disclaimer, the term of this patent is extended or adjusted under 35 U.S.C. 154(b) by 259 days.

(21) Appl. No.: 14/608,278

(22) Filed: Jan. 29, 2015

(65) Prior Publication Data
US 2016/0220141 A1    Aug. 4, 2016

(51) Int. Cl.
*A61B 5/0482*    (2006.01)
*A61B 5/00*    (2006.01)

(52) U.S. Cl.
CPC .......... *A61B 5/0482* (2013.01); *A61B 5/7246* (2013.01)

(58) Field of Classification Search
None
See application file for complete search history.

(56) References Cited

U.S. PATENT DOCUMENTS 6,309,361 B1 * 10/2001 Thornton .............. A61B 5/0484 600/544
2011/0144520 A1 * 6/2011 Causevic ............. A61B 5/0476 600/544

OTHER PUBLICATIONS

Thornton et al.; "Electroencephalogram Biofeedback for Reading Disability and Traumatic Brain Injury;" Child and Adolescent Psychiatric Clinics of North America; 14 (2005) 137-162.*
Thornton; "Exploratory Investigation into Mild Brain Injury and Discriminant Analysis with High Frequency Bands (32-64 Hz);" Brain Injury; Aug. 1999; pp. 477-488.*
Thornton et al.; "The Relation Between Memory Improvement and QEEG Changes in Three Clinical Groups as a Result of EEG Biofeedback Treatment;" Journal of Neurotherapy; May 2013; 17/116-131.*
Thornton et al.; "Traumatic Brain Injury Rehabilitation: QEEG Biofeedback Treatment Protocols;" Appl. Psychophysiol. Biofeedback; Feb. 2009; 34:59-68.*

* cited by examiner

*Primary Examiner* — Daniel J Colilla

(57) ABSTRACT

Mental abilities are labeled with terms such as memory & problem solving and corresponding performance measures (recall score, # correct) can be obtained. The quantitative EEG (QEEG) measure of brain functioning reflects the electrophysiology of the gray & white matter of the brain underlying the scalp. A database of clinical and non-clinical participants underwent a cognitive activation QEEG to determine the relations between the QEEG measures and cognitive performance for memory (auditory and reading) and problem solving. The analysis revealed correlative (positive and negative) relationships between cognitive performance and the Quantitative EEG (QEEG) measures (coherence, phase, magnitude, etc.) during these cognitive activation conditions. An individual can undergo an evaluation and the subject's values on the relevant (and all) variables can be determined. The deficient QEEG variables can be effectively changed with an operant biofeedback conditioning methodology called EEG biofeedback. The method has been shown to improve memory functioning.

3 Claims, 22 Drawing Sheets

Positive Relations

Negative Relations

Fig. 4
Positive Relations
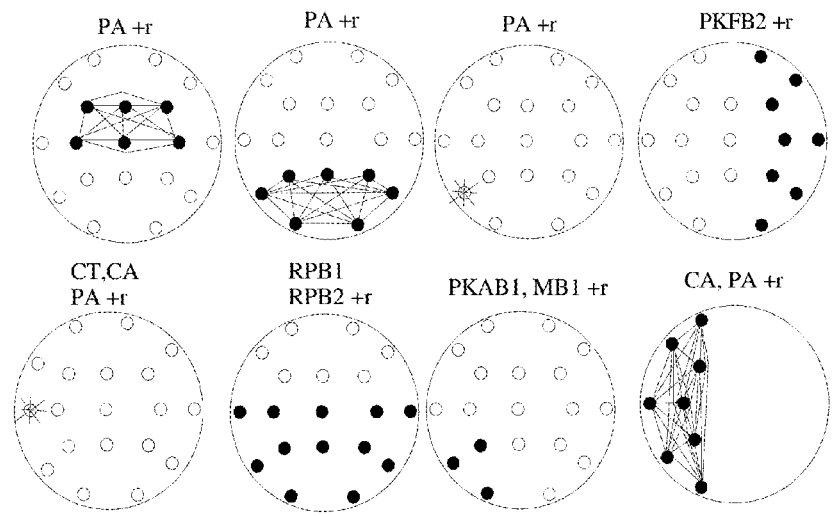
Negative Relations
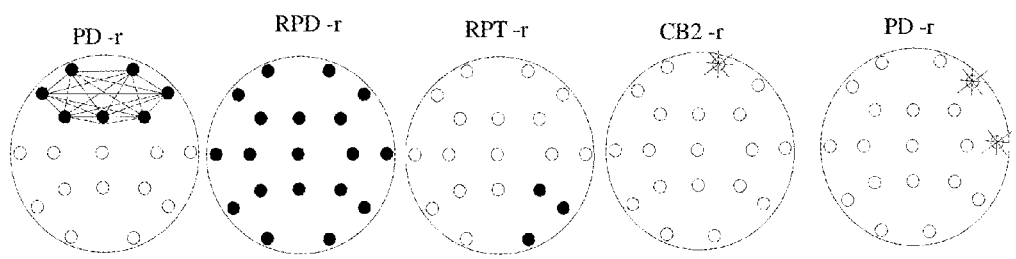

Fig. 5
Positive Relations
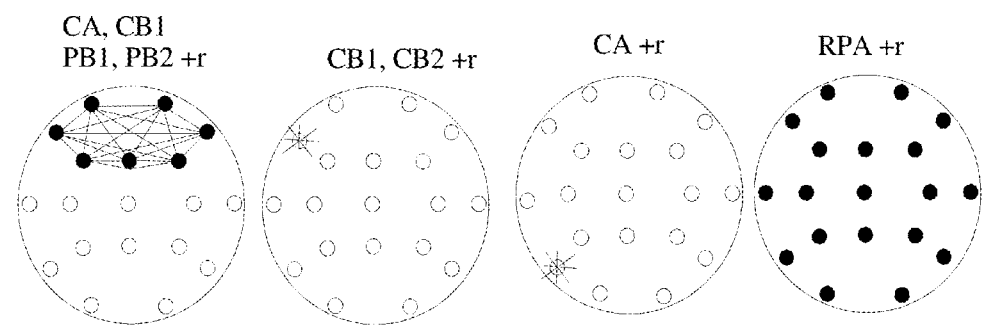
Negative Relations
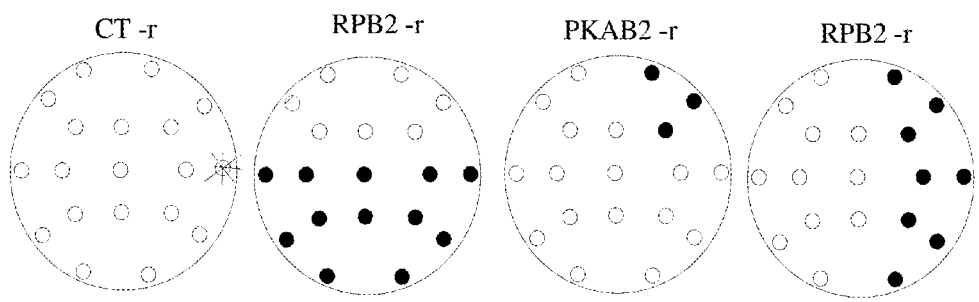

Fig. 6
Positive Relations
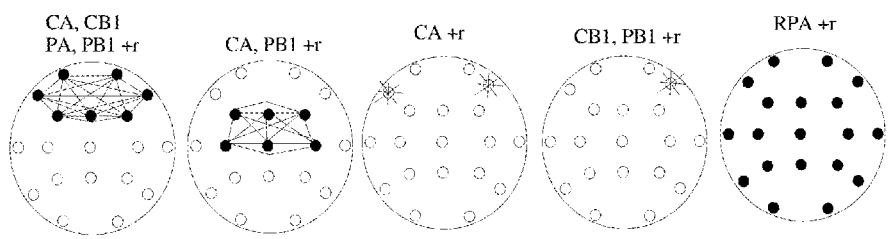
Negative Relations
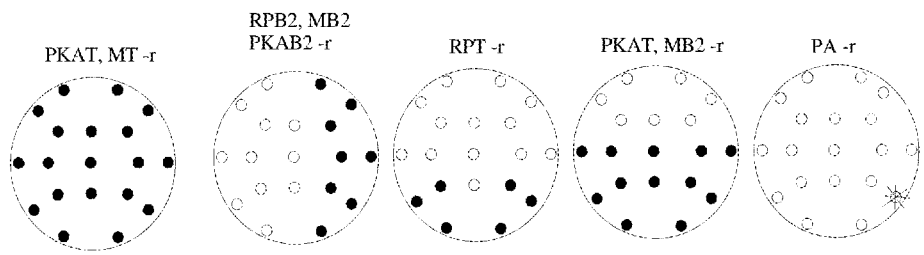

Fig. 7
Positive Relations
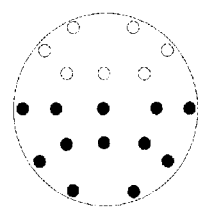
RPB1+r
Negative Relations
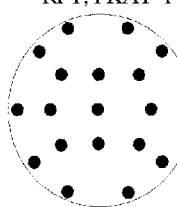 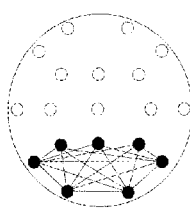 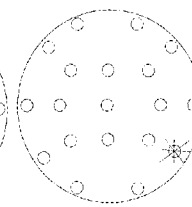 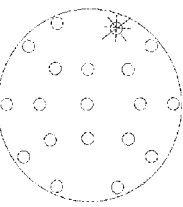 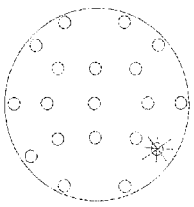
RPT, PKAT -r   CT -r   CT -r   CB2 -r   PA -r Fig. 8
Positive Relations
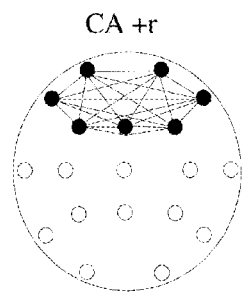
CA +r
Negative Relations
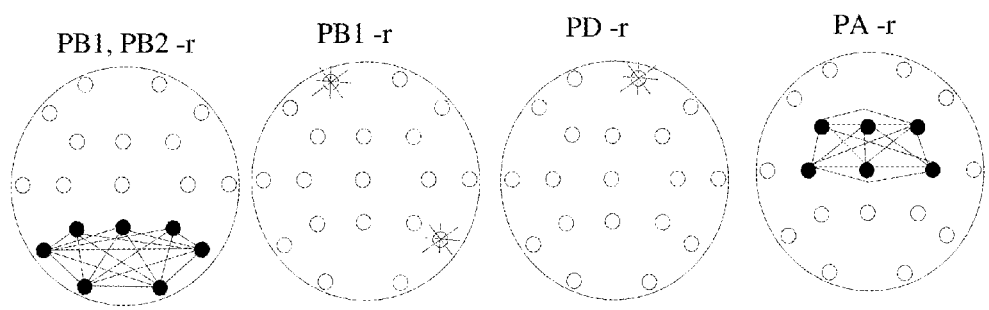
PB1, PB2 -r     PB1 -r     PD -r     PA -r Fig. 10
Positive Relations
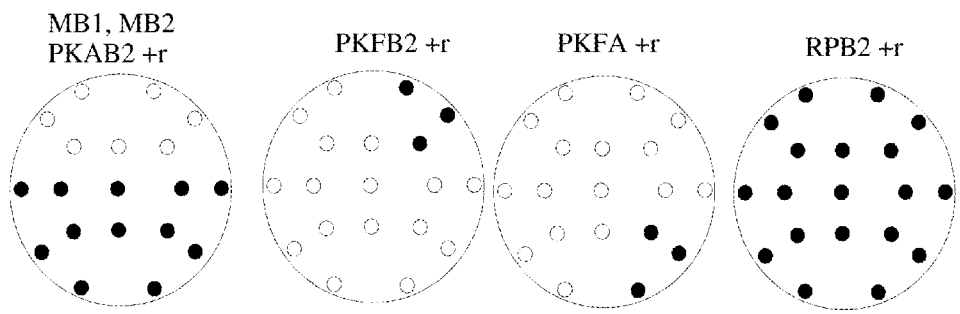
Negative Relations
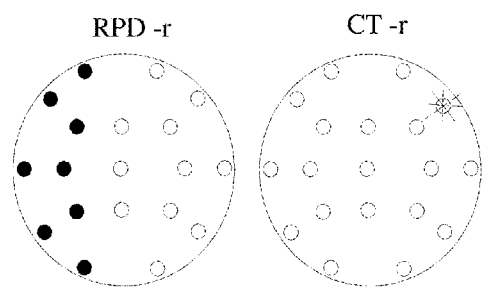

Fig. 11
Positive Relations
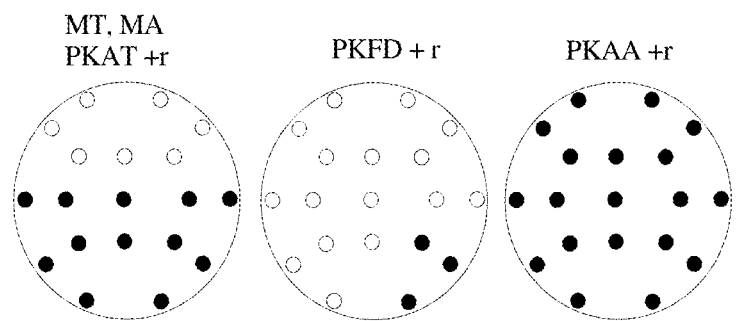
Negative Relations
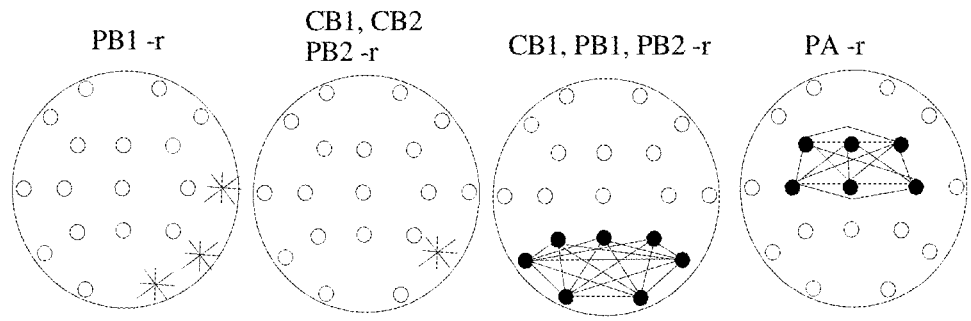

Fig. 12
Positive Relations
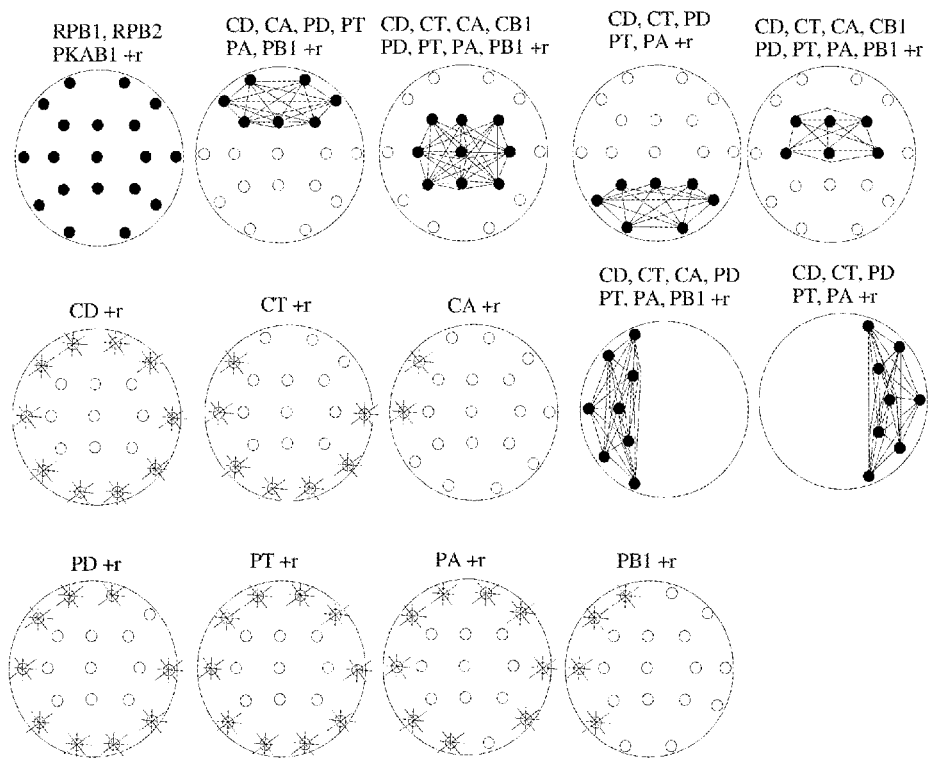
Negative Relations
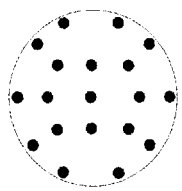

Fig. 13
Positive Relations
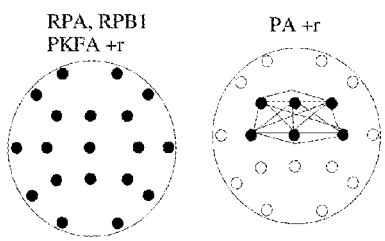
Negative Relations
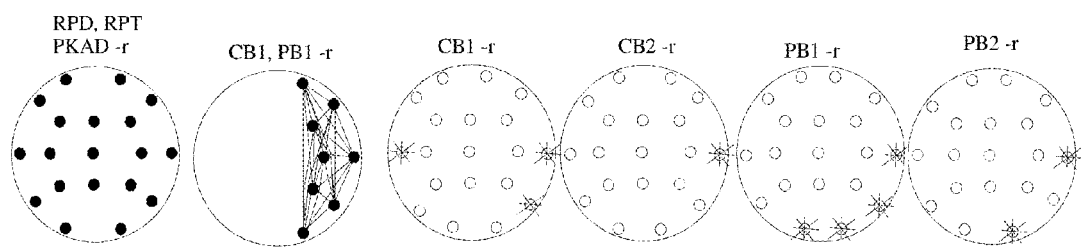

Fig. 14
Positive Relations
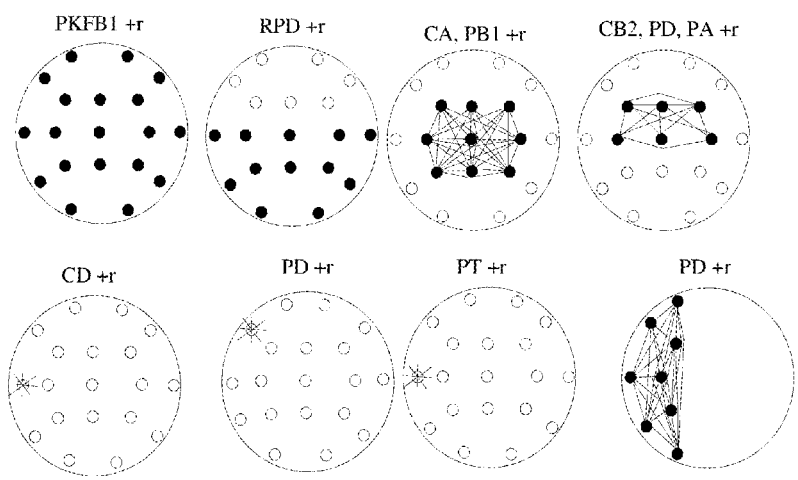
Negative Relations
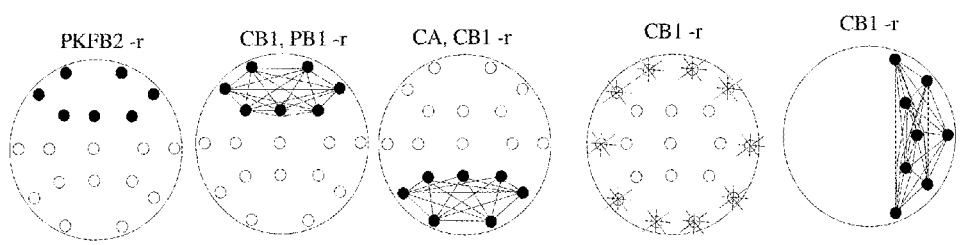

Fig. 16
Positive Relations
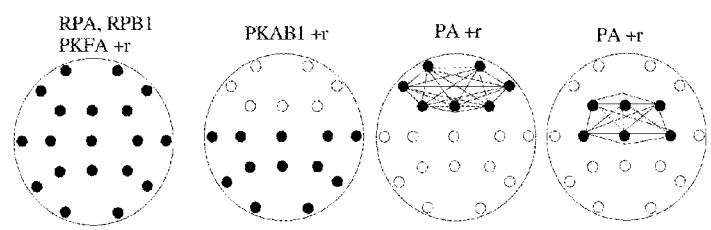
Negative Relations
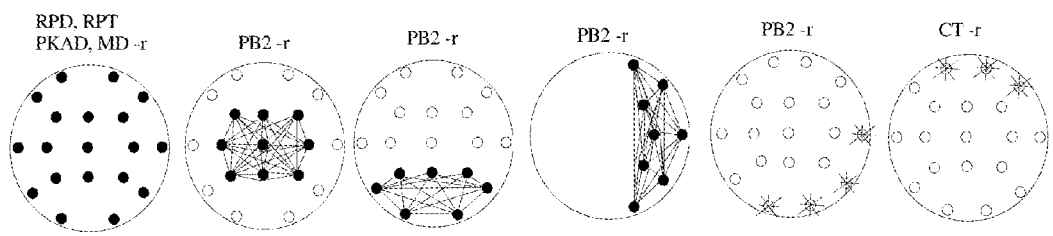

Fig. 18
Positive Relations
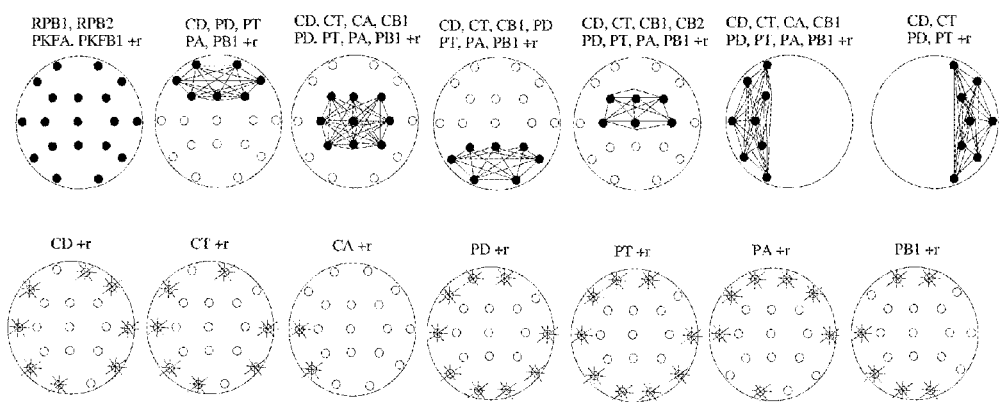
Negative Relations
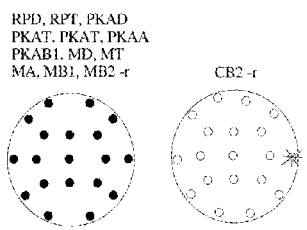

Fig. 19
Positive Relations
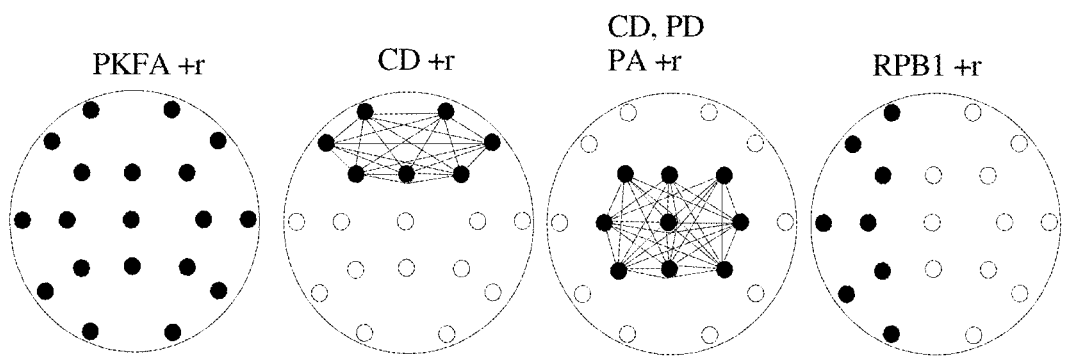
Negative Relations
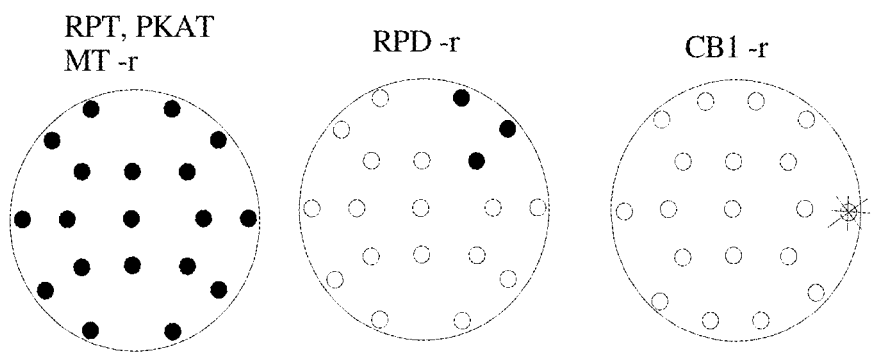

Fig. 20
Positive Relations
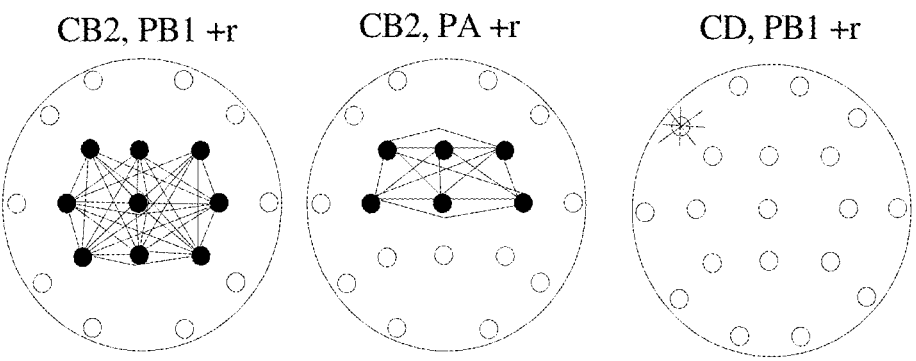
CB2, PB1 +r    CB2, PA +r    CD, PB1 +r
Negative Relations
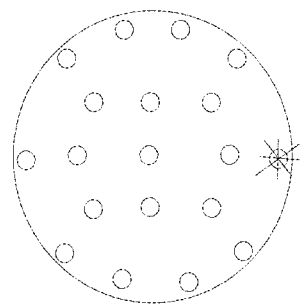
CB2, PB2 -r Fig. 21
Positive Relations
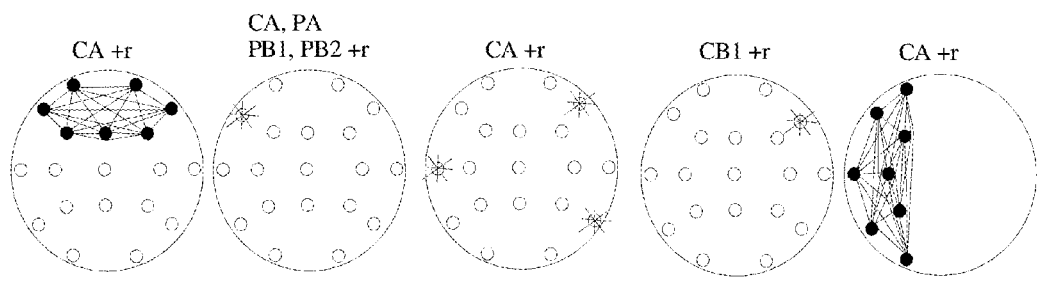
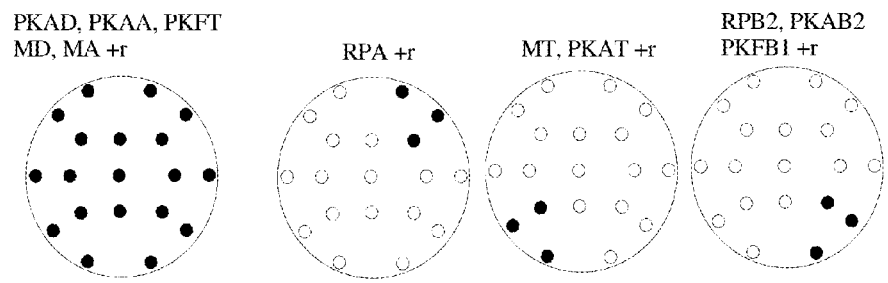
Negative Relations
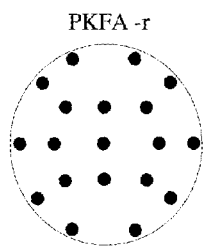

Fig. 22
Positive Relations
RPB1 +r
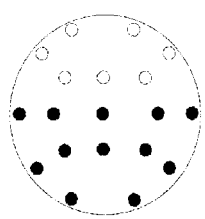
Negative Relations
PKAT -r     RPT, MT +r     CT -r     PT -r     MT -r
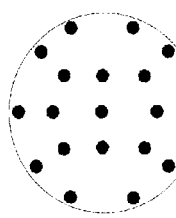 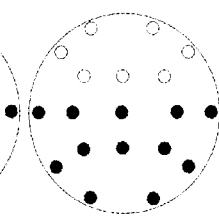 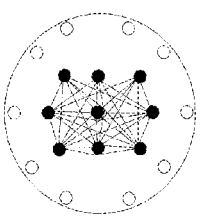 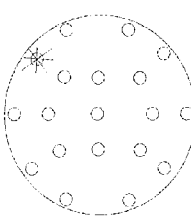 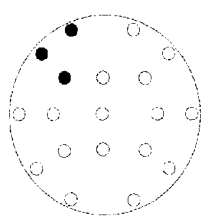

QEEG CORRELATES OF EFFECTIVE COGNITIVE FUNCTIONING—MEMORY AND PROBLEM SOLVING—IN DIVERSE CLINICAL CONDITIONS AND NORMAL POPULATIONS

REFERENCES CITED

U.S. Patent Documents

U.S. Pat. No. 6,309,361 B1 Oct. 30, 2001 Thornton
20090118636 May 7, 2009 Multi-Channel, Multi-Variate Whole-Head Normalization Using Live Z-Scores—Collura
20100094156 Apr. 15, 2010 System and Method for Biofeedback Administration—Collura
20130303933 Nov. 14, 2013 VALIDATION PROCESS FOR IPSATIVE ASSESSMENTS-Collura
20130303934 Nov. 14, 2013 BRAINAVATAR. Collura
2008/0103409 May 2008 Komissarov, Mark

Other Publications

Leuchter, A. F., Cook, I. A., Lufkiln, R. B., Dunkin, J., Newton, T. F., Cumming, J. L, Mackey, J. K. & Walter D. O. (1994). Cordance: A new method for Assessment of cerebral perfusion and Metabolism using quantitative Electroencophalography. Neuroimage, 1, 208.219
Thornton, K. (2002). Rehabilitation of Memory functioning with EEG Biofeedback. Neurorehabilitation, (1), 69-81.
Thornton, K. (2002a). Electrophysiology of Visual Memory for Korean Characters. Current Psychology, Vol. 21, No. 1, 85-108.
Thornton, K. (2002b). Electrophysiology (QEEG) of Effective Reading Memory: Towards a Generator/Activation Theory of the Mind. Journal of Neurotherapy, 6(3), 3 7-66.
Thornton, K. (2000). Electrophysiology of Auditory Memory of Paragraphs. Journal of Neurotherapy, Vol 4(3), 45-73.
Thornton, K. & Carmody, D. (2009). Eyes-Closed and Activation QEEG Databases in predicting Cognitive Effectiveness and the Inefficiency Hypothesis, Journal of Neurotherapy, (13) 1, 1-22.
Thornton, K, Carroll, C. (2010). The Coordinated Allocation of Resource (CAR) Model Intervention for Reading, Problems in two clinics, Neuroconnections, Fall, 8-16.
Thornton, K. & Carmody, D. (2013). The Relation between Memory improvement and QEEG changes in three clinical groups as a result of EEG biofeedback treatment, Journal of Neurotherapy, 17(2). 116-132.
U.S. Pat. No. 6,309,361 B1 Method for Improving Memory by Identifying and Using QEEG Parameters Correlated to Specific Cognitive Functioning—issued Oct. 30, 2001
Thornton, K. (2006). NCLB Goals (and more) are attainable with Neurocognitive Interventions, Vol. 1, Booksurge Press
Thornton, K. & Carmody, D. (2009). Traumatic Brain Injury Rehabilitation: QEEG Biofeedback Treatment Protocols, Applied Psychophysiology and Biofeedback, (34) 1, 59-68.
Thatcher, I. W, North, D., Biver, C., (2002). EEG discriminant analysis of children with learning disabilities: Correlations to school achievement and neuropsychological performance, available at appliedneuroscence.org
Thornton, K. (2000). Electrophysiology of Auditory Memory of Paragraphs. Journal of Neurotherapy, 4(3), 45.73.
Thornton, K. (2002a). Electrophysiology of Visual Memory for Korean Characters. Current Psychology, 21, No. 1, 85-108.
Thornton, K. (2002b). Electrophysiology (QEEG) of Effective Reading Memory: Towards a Generator/Activation Theory of the Mind. Journal of Neurotherapy, 6(3), 3 7.66.
Thornton, K. & Carmody, D. (2009). Eyes-Closed and Activation QEEG Databases in predicting Cognitive Effectiveness and the Inefficiency Hypothesis, Journal of Neurotherapy, (13) 1, 1-22
Thornton, K. & Carmody, D. (2013). The Relation between Memory improvement and QEEG changes in three clinical groups as a result of EEG biofeedback treatment, Journal of Neurotherapy, 17(2). 116-132.
Thornton, K., Carmody, D., (2014) The Coordinated Allocation of Resource (CAR) Electrophysiological Patterns of Recalling Names of Faces in Children, Adolescents and Adults and the Central Processing Unit (CPU) of the Brain, Neuroregulatlon, 1(1), 87-104.
Lexicor Medical Technologies, 753 Broad Street #701, Augusta, Ga. 30901-1380

FIELD OF THE INVENTION

The present invention relates to a novel method for improving memory (auditory and reading) and problem solving for the human brain by measuring, determining, recording, and correlating object-related, quantitative EEG (QEEG) information with the use of whole skull electroencephalography, using a disposable electrode cap connected to a computer system arrangement and more particularly to a method of measuring and determining a large number of meaningful brain electrical activity levels in response to memory material (presented via auditory and visual modalities) and non-verbal material involving problem solving tasks. The method involves recording a subject's baseline values on QEEG values while they are engaged in one of the three cognitive tasks. The QEEG data is transformed to ASCII data which is then analyzed by software. The subject's performance is compared to an appropriate database of subjects who underwent similar evaluations. The appropriate databases are comprised of all of the sample (A: all ages, all clinical and non-clinical conditions; B: all non-clinical children under the age of 14; C: all non-clinical adolescents and adults over the age of 14). If the subject is a non-clinical child under the age of 14 then the appropriate database is B, etc. All of the QEEG differences between the subject and the appropriate database are available for analysis. However, the focus of the analysis is on the QEEG variables which have positive and negative relations to the cognitive performance in the appropriate database. EEG biofeedback treatment protocols are determined by the subject's deviation from the average value in the database on the variables which are positively and negatively related to the performance variables. Once the differences from the relevant database are determined, appropriate treatment protocols are employed with the subject to increase the values of the variables positively related to performance and decrease the values of the variables negatively related to performance. The treatment consists of the operant conditioning (auditory and visual feedback) of the EEG signal to improve the subject's values on the relevant deficient variables to improve their cognitive functioning (memory or problem solving) by employing EEG biofeedback software. For example, the spectral correlation coefficient (coherence) values of alpha from the left temporal location (T3) to all other 18 locations is positively correlated with auditory memory performance in the non-clinical children. If a subject is under the age of 14, then the subject's value would be compared to the children's database for the average T3 coherence alpha relationship value to each of the other 18 locations. If the subject's value between T3 and F3, for example, is below the average value, then that connection becomes the focus of the EEG biofeedback intervention, which has the goal of increasing the value of the variable to the average value or above. The figures present the linear relationships between the QEEG variables and performance. Thus, the higher the value of the variable the better the performance. Thus, the goal is to increase the value of the variable to at least the average value, preferably above. Similarly if a variable, such as theta relative power in a particular location, is negatively related to memory performance and the subject's value is above the average value (in the appropriate database) then the focus of the EEG biofeedback intervention is to lower the value of the theta relative power variable to the point of being at the average value or below. As the relation is a linear relationship between the QEEG variable and performance, the goal is to lower the variable to at least the average value, preferably below.

The FIGS. 3-22 provided indicate the positive and negative correlations between the QEEG variables and performance for the respective groups.

DESCRIPTION OF THE PRIOR ART

The research in the area of cognitive functioning and brain physiology is of two general types, blood flow related and electrical activity. Studies of electrical activity address event-related potentials (ERP) or quantitative EEG measures. ERP's study the activity of the brain within milliseconds following exposure to a stimulus. QEEG studies employ a longer period of time for analysis. The relationship between blood flow and electrical activity has been researched with varied findings. Leuchter, A. F., Cook, I. A., Lufkin, T. B., Dunkin, J., Newton, T. F., Cummings, J. L., Mackey, J. K. & Walter, D. O. (1994) also noted that the associations between EEG power and perfusion or metabolism vary considerably across frequency bands and sites, with some studies showing little or no association.

Within the field of biofeedback applications to problems in human functioning, there is a subspecialty, commonly referred to as Neurotherapy. Neurotherapy is the providing of electrophysiological information (in the form of the QEEG parameters) to a subject for the purpose of changing the parameter being measured. This type of biofeedback has been successfully employed in the remediation of Attention Deficit Disorder, the elevation of IQ scores 15 to 25 points, addictive conditions such as alcoholism, and emotional problems such as depression, post-traumatic Stress disorder and anxiety.

While these results have been empirically impressive, they have not been based upon a complete theoretical orientation and/or empirical base of brain electrophysiology. The research has primarily focused on the C3-Cz locations (ADD and Learning Disabilities) and occipital leads (alcoholism) and have addressed issues of reducing theta and/or increasing alpha or beta activity (depending upon the problem).

The pattern of previous research findings regarding the relationship between cognition and the QEEG implies that cognitive abilities reside in increased beta (13-21 Hz) activity, decreased theta and delta activity. However, the findings are not consistent across cognitive tasks and populations and did not correlate specific QEEG variables during the task with performance for all locations and frequencies extending to the 64 Hz range. The confusing pattern of results is due to the different algorithms, different tasks, different populations and different methodologies.

BACKGROUND/SPECIFICATIONS

Research addressing EEG biofeedback (Neurotherapy) has grown considerably in the past two decades. EEG biofeedback addresses the quantitative EEG (QEEG) signal in an operant conditioning (rewarding/inhibiting of spontaneous behavior) model. It has been amply demonstrated that this intervention approach can change the electrophysiological signals of the QEEG (Thornton & Carmody, 2013; Thornton & Carroll, 2010). However, there are some 2100 variables involved in the QEEG signal (involving 19 locations and 5 frequencies (0-64 Hz)). The determination of what signal to reward or inhibit has predominantly fallen upon the individual practitioner to decide. What the field is grossly lacking is the definition of what cognitive/behavioral skills are determined by what QEEG variable, which is the focus of this patent. This patent addresses 3 cognitive skills (auditory memory, reading memory, problem solving) and shows what QEEG variables are related (positively and negatively) with performance variables, thus providing the empirical basis for decision making in this area.

The search for the relations between the quantitative EEG variables and cognitive performance have been the focus of research efforts such as Thatcher et al. (2002) and others. The purpose of understanding these relations was to provide a sound empirical base for EEG biofeedback interventions. All of the research in this area has focused on the relation between eyes closed data or simple activation tasks and subsequently (different time) obtained cognitive performance. Thornton & Carmody (2009) successfully challenged this assumption and demonstrated that the meaningful QEEG correlates can only be obtained if the subject is actively engaged in a specific cognitive task which assesses a specific cognitive skill.

The specifics of EEG biofeedback have been the focus of the four US patent applications by T. Collura, without specifying what QEEG variables are relevant to what cognitive skill. The focus of these patents was on employing eyes closed or simple activation measures (such as opening the subjects eyes) and pursuing intervention protocols which train the subject to obtain normative values in reference to eyes closed data. This patent is not claiming to be a biofeedback device but rather the knowledge of how the biofeedback device can most effectively be employed. Biofeedback technology has been adequately described in the Collura applications and doesn't require replication in this application. The invention described in this patent application can be employed by any hardware or software manufacturer in the QEEG field, if the appropriate algorithms are implemented. The format of the patent application is the same as employed in the U.S. Pat. No. 6,309,361 B1 Oct. 30, 2001 patent by Thornton.

Komissarov (patent 2008/0103409) claims "A method for altering a visual cognitive ability in a human comprising: (a) eliciting the human to imagine that he or she possesses an optical sensory ability that operates when the human is sight-deprived; (b) presenting the sight-deprived human with an optical sensory stimulus for a time sufficient that the human perceives the presence of the optical stimulus; and (c) eliciting, within a few seconds of the human perceiving the presence of the optical stimulus, a description of the optical stimulus, so as to thereby alter the visual cognitive ability of the human." The inventor did report "On the other hand, there was a mysterious, clear and replicated VEP in condition B" (blindfold simulated reading condition). The claim does not present any information relating the VEP or QEEG variables to performance issues.

The search for the specific quantitative EEG correlates of specific cognitive abilities under cognitive activation conditions (in non-clinical participants and clinical subjects) has been the subject of much of the inventor's research publication history. However, only a few of these publications (Thornton, 2000, 2002a, 2002b, 2006, 2009, 2014) have presented the actual QEEG correlates of successful and unsuccessful cognition and have focused on the auditory and reading memory tasks. None have presented the information in the form it is presented in this patent application, with the use of processing units and flashlights. Research on the Ravens Matrices has not yet been published by the investigator. In addition, the investigator has increased the activation database considerably and has included clinical participants in the research (in comparison to the Thornton 2001 patent).

Thornton & Carmody (2009) reported on the problems of using eyes closed data in understanding the actual relations between the QEEG and cognition under cognitive task conditions. The study indicated that the relative power values of theta activity in the eyes closed condition correlated positively with subsequent auditory recall. However, the relative power of theta values are 1) generally considered a negative indicator of cognitive ability and 2) did not correlate with successful performance during the actual task. The article further elaborated on many of the inconsistencies between eyes closed and simple attention tasks (visual, auditory) predictor QEEG variables and subsequent cognitive task QEEG correlates to auditory memory and reading memory. The article concluded that eyes closed data and even simple visual and auditory attention tasks are not useful in understanding or meaningfully predicting what occurs under task conditions. In addition, almost all currently employed databases do not extend the frequency range up to 64 Hertz. The higher "gamma" (32-64 Hz) frequency range is employed in the data presented. The value of the information resides in its application in the EEG biofeedback field. Thornton & Carmody (2013) documented that application of this type of information and EEG biofeedback results in improvements in auditory and reading memory averaging 1.78 standard deviations across a group of 86 participants (normal, learning disabled and brain injured). All the groups were performing better than the normative reference group at the end of their treatment (average of 45 sessions).

BRIEF SUMMARY OF THE INVENTION

This patent designates the critical Quantitative EEG (QEEG) variables for 3 cognitive skills (auditory memory, reading memory, problem solving) and makes 3 claims regarding these skills. The World English Dictionary defines invention in patent law as "the discovery or production of some new or improved process or machine that is both useful and is not obvious to persons skilled in the particular field." The improved process in this patent application is the knowledge of specific QEEG correlates of effective cognitive functioning of specific cognitive skills which can be employed in EEG biofeedback intervention protocols.

EEG biofeedback involves the operant conditioning of the EEG signal. The relationship between specific QEEG variables and specific cognitive skills during specific cognitive tasks has not been established. The claim is a process to improve an individual's specific cognitive abilities by identifying the QEEG variables which are related to specific skills. A participant's values on the critical variables is obtained during a cognitive activation QEEG evaluation and a comparison to a relevant database is conducted. The participant then undergoes EEG biofeedback to improve the value of the relevant QEEG variable, resulting in improved cognition. The claims are not claiming specific QEEG variable but rather the relationship of a QEEG variable to performance, an individual's relationship to the database on that variable and the value of improving the value of the variable for specific cognitive skills.

The employment of this knowledge has been shown to improve memory functioning (auditory and reading memory) an average of 1.78 standard deviations across a group of 86 participants (normals, learning disabled and brain injured) to the point that all groups were functioning better than their respective normative control group values (Thornton & Carmody, 2013).

BRIEF DESCRIPTION OF THE DRAWINGS

Group (A) includes all subjects (clinical and non-clinical and all ages); Group (B) consists of all non-clinical child participants (under the age of 14); Group (C) consists of non-clinical adolescents and adults (over the age of 14);

FIG. 4 presents the reading QEEG correlates for Group B (all non-clinical children);

FIG. 5 presents QEEG correlates for Group C (non-clinical adolescents and adults during input reading task);

FIG. 6 presents QEEG correlates for all subjects (Group A) during immediate reading recall task;

FIG. 7 presents QEEG correlates for non-clinical children (Group B) during immediate reading recall;

FIG. 8 presents QEEG correlates for non-clinical adolescents and adults (Group C) during immediate reading recall task;

FIG. 10 presents QEEG correlates for non-clinical children (Group B) during delayed reading recall task;

FIG. 11 presents QEEG correlates for non-clinical adolescents and adults (Group C) during delayed reading recall task;

FIG. 12 presents QEEG correlates for all (Group A) during auditory memory task—input condition;

FIG. 13 presents QEEG correlates for children (Group B) during auditory memory task input condition;

FIG. 14 presents QEEG correlates for adolescents and adults (Group C) during auditory memory task—input condition;

FIG. 16 presents QEEG correlates for children (Group B) during auditory immediate recall;

FIG. 18 presents QEEG correlates for all participants (Group A) during delayed auditory memory recall task;

FIG. 19 presents QEEG correlates for non-clinical children (Group B) during delayed auditory memory recall task;

FIG. 20 presents QEEG correlates for non-clinical adolescents & adults (Group C) during delayed auditory memory recall task;

FIG. 21 presents QEEG correlates for adolescents and adults (Group C) during Ravens Progressive Matrices; and FIG. 22 presents QEEG correlates for children (Group B) during Ravens Progressive Matrices.

DETAILED DESCRIPTION OF THE METHOD EMPLOYED TO OBTAIN THE IMPROVED PROCESS APPROACH AND RESULTS OBTAINED

Table 1 presents the information on the present sample size for the child, adolescent and adult sample (clinical and non-clinical participants).

TABLE 1

Children, Adolescents, & Adult

|  | Listening Condition | Reading Condition | Problem Solving |
|---|---|---|---|
| Avg. Age | 28.01 | 27.6 | 28.8 |
| Age Range (Mos.) | 68-921 | 68-921 | 93-869 |
| Educ. | 11.5 | 11.4 | 11.14 |
| Male | 184 | 176 | 60 |
| Female | 148 | 130 | 56 |
| Total | 332 | 306 | *1062 |

*= indicates total number of Ravens matrices tasks administered

The Thornton (2001) patent had a subject pool of 83 normal adults and 30 children under the age of 13. The present subject pool is approximately 332 children, adolescents and adults. The 2001 patent only employed normal subjects in the analysis. This sample included all available subjects, including those with brain injuries, learning problems, attention deficit disorder and other clinical conditions not necessarily categorized with these labels (i.e. radiation treatment for cancer). Thus, the sample size represents almost a 300% increase in size.

Apart from the issue of the increase in sample size is the issue of greater generalizability of the present results and increase in face validity. The generalizability argument is based upon the inclusion of the diverse set of clinical conditions. Thus, a variable which may not be relevant in a normative sample may be critical in a learning disabled sample.

The patent addresses three specific cognitive skills 1) Auditory Memory; 2) Reading Memory; 3) Problem Solving, across the age range of 5.6 to 76.7 years. For each of the memory tasks, the data is analyzed according as to whether it was recorded during the input part (while listening or reading) and immediate recall part. The immediate recall tasks involves the subject quietly recalling the information while their eyes are closed. For the Raven's task only the data obtained during the administration of the task is analyzed for non-clinical children, adolescents and adults.

The respective data is analyzed according to whether the variables are positively or negatively correlated with the performance variable. The alpha level was set to 0.05. Three groups were available for analysis for analysis. The first group (A) included all subjects (clinical and non-clinical and all ages). The second group (B) consisted of all non-clinical child participants (under the age of 14). The third group (C) consisted of non-clinical adolescents and adults (over the age of 14).

Theoretical Concepts

Figure 2:
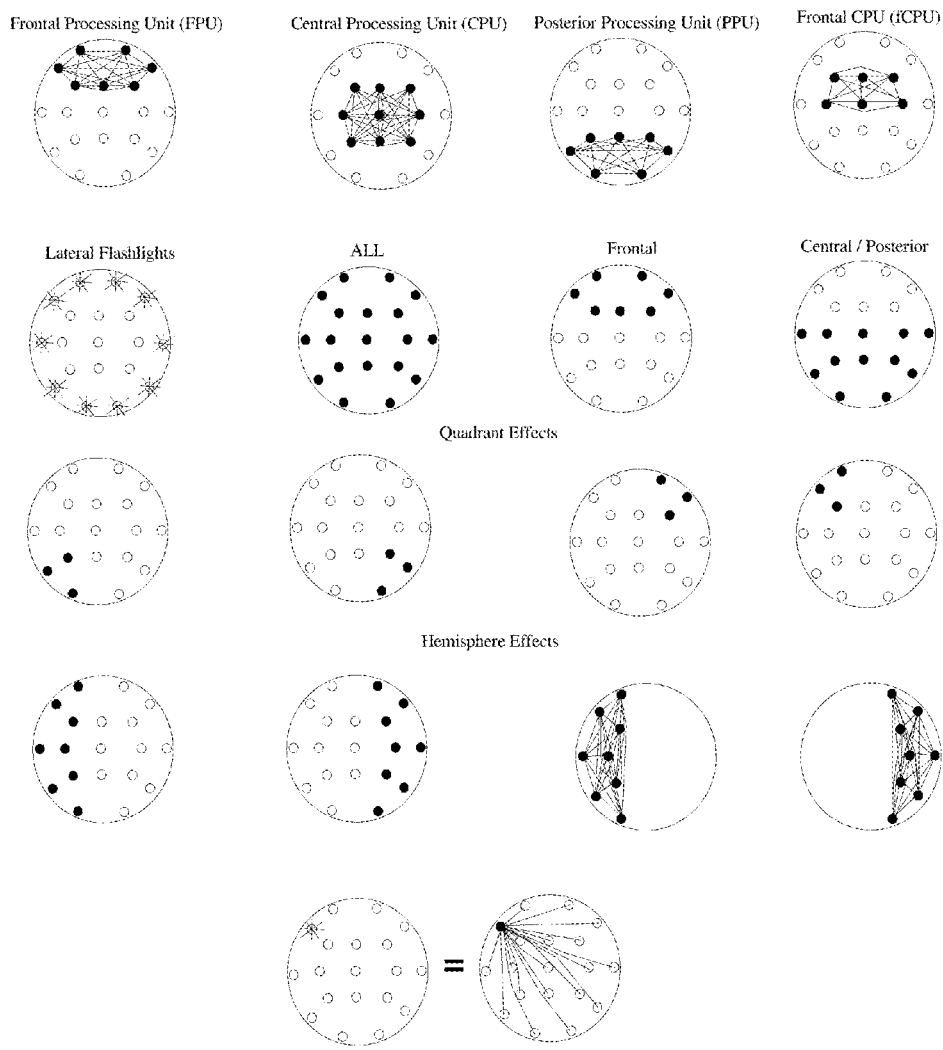
FIG. 2 presents the analysis grouping of the variables.

The results of the analysis are consistent with the Coordinated Allocation of Resource (CAR) model of brain functioning. The model states that effective and non-effective electrophysiological functioning is a result of the allocation of specific sets of the brain's resources, which can be overlapping across different cognitive tasks. The model employs a flashlight metaphor which states that a specific location can send out a "beam" to all other locations within a frequency or operate as a mini-flashlight which involves several receiving locations but not all locations. An additional theoretical construct employed in the model is that there is a heuristic Processing Unit. The frontal processing unit (FPU) consists of the coherence and phase relations between the following locations: Fp1, Fp2, F7, F8, F3, Fz, F4). The central processing unit involves the F3-Fz-F4; C3-Cz-C4; P3-Pz-P4 locations. The posterior processing unit (PPU) involves P3-Pz-P4, T5, T6, O1, & O2. In addition, the employment of a frontal CPU (fCPU) (F3-Fz-F4; C3-Cz-C4) is employed. In addition, to the processing units the flashlight locations are indicated in the figures by the star figure. Each star location indicates that the location is sending out a signal (within a specific frequency) to all other locations, as indicated in FIG. 2 (lateral flashlights). FIG. 2 presents the analysis grouping of the variables.

The concept of coherence employs the Lexicor's algorithm of Spectral Correlation Coefficients and Lexicor's Phase algorithm. Different hardware/software manufacturers employ different algorithms to calculate these values but are all based on similar concepts, which are claimed in this patent. The following measures were available for the analysis. The following text describes the QEEG variables involved in the analysis.

Arousal Measures

Absolute Magnitude: the average EEG magnitude (as defined in microvolts) within a frequency band over a specific time period (epoch).

Relative Magnitude: the relative EEG magnitude within a frequency band (absolute magnitude in a particular band divided by the total microvolts generated at a particular location in all bands)

Peak Amplitude: the peak amplitude of a frequency band during an epoch of time (defined in microvolts) Peak Frequency: the peak frequency within a band during an epoch of time (defined in_frequency)

Peak Frequency: the peak frequency within a band during an epoch of time (defined in frequency)

Connectivity Measures Coherence: the average similarity between the waveform morphology in a particular frequency band from two locations over an epoch (a one-second period of time in this research). The measure has been conceptualized as the strength/number of connections between the two locations. Lexicor software provides an amplitude matching algorithm. However, an alternate conceptualization of the relations (SCC and phase) could refer to the quality of signal transmission, with degradation of the signal reflected in lower values.

Phase: the time lag between waves from two locations in a particular band as defined by how soon after the beginning of an epoch a particular waveform at location #1 is matched in location #2 (amplitude)

Frequency Ranges

The frequency range employed is 0-64 Hertz. The 5 frequency bands are defined as follows:

Delta: 0-4 Hz Theta: 4-8 Hz Alpha: 8-13 Hz

Beta1: 13-32 Hz Beta2: 32-64 Hz

Nomenclature

The following nomenclature is employed to refer to the different frequencies and variables.

CD=Coherence Delta; CT=Coherence Theta; CA=Coherence Alpha; CB1=Coherence Beta1; CB2=Coherence Beta2 PD=Phase Delta; PT=Phase Theta; PA=Phase Alpha; PB1=Phase Beta1; PB2=Phase Beta2 RPD=Relative Power Delta; RPT=Relative Power Theta; RPA=Relative Power Alpha; RPB1=Relative Power Beta1; RPB2=Relative Power Beta2 MD=Magnivolts Delta; MT=Magnivolts Theta; MA=Magnivolts Alpha; MB1=Magnivolts Beta1; MB2=Magnivolts Beta2 PKFD=Peak Frequency Delta; PKFT=Peak Frequency Theta; PKFA=Peak Frequency Alpha; PKFB1=Peak Frequency Beta1; PKFB2=Peak Frequency Beta2 PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

Figure 1:
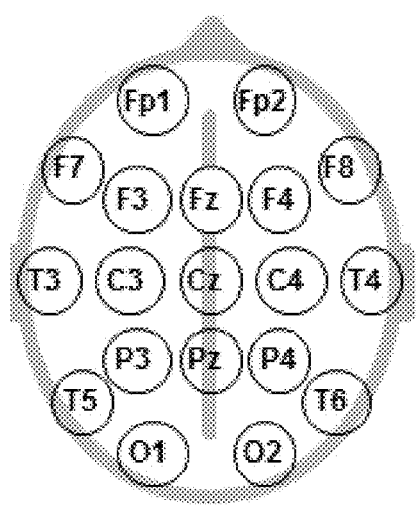
FIG. 1 presents the standard locations in the 10-20 system.

FIG. 1 presents the standard locations in the 10-20 system.

10-20 Nomenclature for EEG locations

FIG. 2 presents the variables that are employed in the analysis.

Summary of Specific Claims

This patent addresses the relations between the quantitative EEG (QEEG) variables and the mental abilities of auditory and reading memory as well as problem solving ability, as assessed by the Ravens matrices (a well accepted measure of intelligence). The QEEG variables examined were the "arousal" variables of magnitude, relative power, peak amplitude, & peak frequency while the connection variables involved Spectral Correlation Coefficients (SCC) and phase relations. The analysis presented in the figures document the significant positive and negative relations between the QEEG variables and performance on the cognitive task during the input and recall tasks (for auditory and reading memory) and during task performance on the Ravens matrices. The three claims made involve 1) the QEEG correlates of reading memory (input, immediate & delayed recall) for groups A (all), B (non-clinical children under the age of 14), & C (non-clinical adolescents and adults over the age of 14); 2) the QEEG correlates of auditory memory (input, immediate & delayed recall) for groups A, B, & C; 3) the QEEG correlates of problem solving for group B & C.

Task Methodology—Reading

The following text describes the data collection method. The reading task involves the subject reading for 100 seconds (a full page of a story about a Kleenex factory). The subject reads the page for 100 seconds, then closes their eyes and quietly recalls the story to themselves for 50 seconds and then tells the examiner outloud what they recalled during the quiet recall period. About 15-20 minutes later the subject is asked to close their eyes and recall the story that they had previously read (Kleenex factory). After 50 seconds of quiet recall the subject is requested to tell the examiner what they recalled during the quiet period. The total memory score refers to the immediate recall and the delayed recall combined.

The analysis of the relations between reading memory functioning and the QEEG variables can vary according to the group that is being analyzed (age, clinical, non-clinical). The figures present those variables that are significantly related across the different groupings of the participants previously discussed (groups A, B, & C). The line connecting two locations indicate a significant relation (for coherence and phase relations). A location which is significant (arousal variables) is indicated by a black circle. The frequencies and variables involved in the figure are indicated at the top of the figure.

Figure 3:
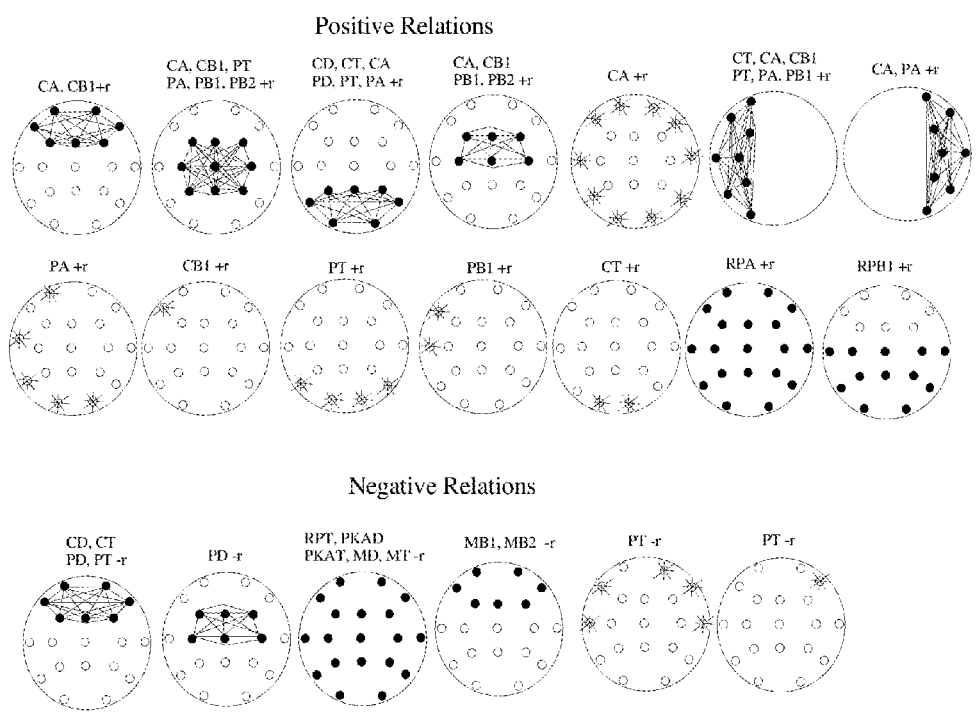
FIG. 3 presents the reading QEEG correlates for Group A (all ages and all conditions (clinical, non-clinical))

FIG. 3 presents the data for group A (all subjects, all ages). The figure indicates significant involvement (negative and positive) of the SCC and phase relations across the 5 frequencies and involvement of the arousal variables across all frequencies.

FIG. 3—Reading QEEG correlates for Group A (all ages and all conditions (clinical, non-clinical)

In FIG. 3 the variables are defined as:

CD=Coherence Delta; CT=Coherence Theta; CA=Coherence Alpha; CB1=Coherence Beta1; PD=Phase Delta; PT=Phase Theta; PA=Phase Alpha; PB1=Phase Beta1; PB2=Phase Beta2; RPT=Relative Power Theta; RPA=Relative Power Alpha; RPB1=Relative Power Beta1; MD=Magnivolts Delta; MT=Magnivolts Theta; MB1=Magnivolts Beta1; MB2=Magnivolts Beta2; PKAD=Peak Amplitude Delta; PKAT=Peak Amplitude Theta FIG. 4 shows the QEEG correlates during the input task with reading memory for non-clinical children. The figure shows the importance of PA, PKFB2, RPB1, RPB2, and left posterior PKAB1 & MB1. Negative correlates involve RPD, FPU (PD), right posterior RPT and Fp2 CB2.

FIG. 4—Reading QEEG correlates for Group B (all non-clinical children)

In FIG. 4 the variables are defined as:

CT=Coherence Theta; CA=Coherence Alpha; CB2=Coherence Beta2; PD-Phase Delta; PA=Phase Alpha; RPD=Relative Power Delta; RPT=Relative Power Theta; RPB1=Relative Power Beta1; RPB2=Relative Power Beta2; MB1=Magnivolts Beta1; PKFB2=Peak Frequency Beta2; PKAB1=Peak Amplitude Beta1

FIG. 5 shows the QEEG correlates during reading with the total reading score for the non-clinical adolescent and adult group (Group C). As the figure indicates the significant predictors involve the FPU (CA, CB1, PB1, PB2), F7 CB1 & CB2 and all locations for RPA. Variables negatively associated with performance involve RPB2, PKAB2 and T4 CT.

FIG. 5—QEEG correlates for Group C (non-clinical adolescents and adults during input reading task)

In FIG. 5 the variables are defined as:

CT=Coherence Theta; CA=Coherence Alpha; CB1=Coherence Beta1; PB1=Phase Beta1: PB2 Phase Beta2; RPA=Relative Power Alpha, RPB2=Relative Power Beta2; PKAB2=Peak Amplitude Beta2

FIG. 6 shows the QEEG correlates with reading recall during the immediate recall in Group A. As the figure indicates the FPU (CA, CB1, PA, PB1), CPU (CA, PB1) and all locations for RPA along with flashlight activity involving CA from F7 & F8 and F8 (CB1, PB1) are the main contributors to performance. The negative relations involve theta variables (PKAT, MT, RPT) and beta2 (RPB2, MB2, PKAB2) and T6PA.

FIG. 6—QEEG correlates for all subjects (Group A) during immediate reading recall task In FIG. 6 the variables are defined as:
CA=Coherence Alpha; CB1=Coherence Beta1; PA=Phase Alpha; PB1=Phase Beta1; RPT=Relative Power Theta; RPA=Relative PowerAlpha; RPB2=Relative Power Beta2; MT=Magnivolts Theta; MB2=Magnivolts Beta2; PKAT=Peak Amplitude Theta; PKAB2=Peak Amplitude Beta2

FIG. 7 shows the QEEG correlations with performance during the immediate reading recall task for Group B (non-clinical children). The figure indicates the sole significant positive predictor involving posterior RPB1, while theta (RPT, PKAT), PPU (CT), T6CT, Fp2CB2 and T6PA had negative influences.

FIG. 7—QEEG correlates for non-clinical children (Group B) during immediate reading recall task In FIG. 7 the variables are defined as:
CT=Coherence Theta; CB2=Coherence Beta2; PA-Phase Alpha; RPT=Relative Power Theta; RPB1=Relative Power Beta1; PKAT=Peak Amplitude Theta FIG. 8 shows the QEEG correlates with reading recall performance during the immediate recall task. As the figure indicates the FPU (CA) was the sole determinant of performance while negative influences involve PPU (PB1, PB2), fCPU (PA) and flashlight involving PB1 (Fp1, T6) and Fp2 (PD).

FIG. 8—QEEG correlates for non-clinical adolescents and adults (Group C) during immediate reading recall task In FIG. 8 the variables are defined as:
CA=Coherence Alpha; PD=Phase Delta; PA=Phase Alpha; PB1=Phase Beta1; PB2=Phase Beta2

Figure 9:
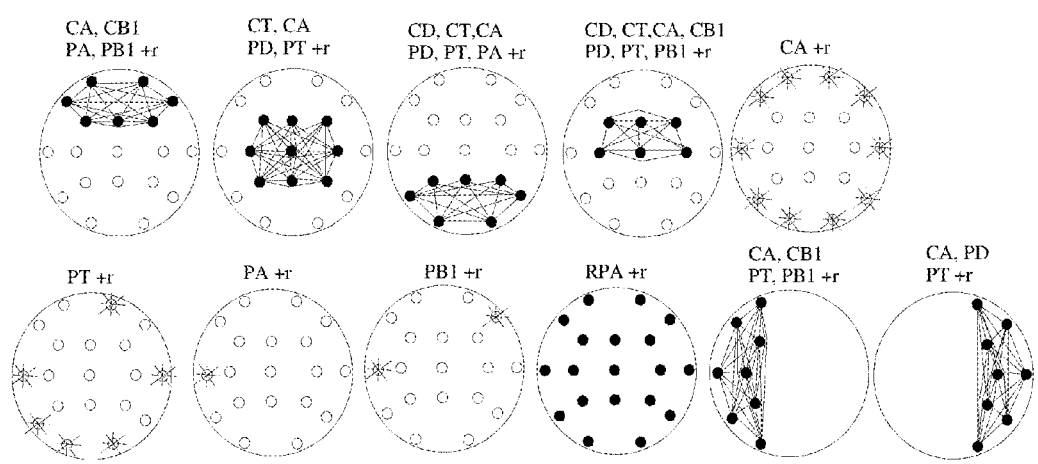
FIG. 9 presents QEEG correlates for all participants (Group A) during delayed reading recall task.

FIG. 9 shows the QEEG correlates of delayed reading recall for Group A (all participants). The figure shows diffuse SCC and phase involvement involving the delta to beta1 frequencies, with a dominant flashlight pattern of CA and PT and a dominant left hemisphere involvement of CB1 and PB1. The positive arousal variable is RPA while the negative indicators involve all locations for the lower frequencies (0-8 Hz), PKAB1, PKAB2, & MB2. Additional negatively related to performance variables involve frontal beta activity (MB1), central/posterior RPD & RPT and right frontal RPB2.

FIG. 9—QEEG correlates for all participants (Group A) during delayed reading recall task In FIG. 9 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPA; Relative Power Alpha; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFD=Peak Frequency Delta; PKFT=Peak Frequency Theta; PKFA=Peak Frequency Alpha; PKFB1=Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

FIG. 10 shows the QEEG correlates with the delayed reading memory score during the delayed recall reading task for Group B. The figure indicates positive involvement of central/posterior MB1, MB2, PKAB2, all locations for RPB2, right posterior PKFA and right frontal PKFB2. The variables negatively related to performance involve left hemisphere locations for RPD and the CT flashlight from F8.

FIG. 10—QEEG correlates for non-clinical children (Group B) during delayed reading recall task In FIG. 10 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPA; Relative Power Alpha; RPB1=Relative Power Beta1; RPB2=Relative Power Beta2 MD=Magnivolts Delta; MT=Magnivolts Theta; MA=Magnivolts Alpha; MB1=Magnivolts Beta1; MB2=Magnivolts Beta2; PKFB2=Peak Frequency Delta; PKFA=Peak Frequency Theta; PKFA=Peak Frequency Alpha; PKFB1 Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

FIG. 11 shows the QEEG correlates with the delayed reading memory score (Group C) during the task. The figure indicates positive relations with memory for all locations of PKAA, right posterior PKFD and central/posterior MT, MA, & PKAT. The variables negatively related to performance were the posterior processing unit (CB1, PB1, PB2), frontal CPU (PA), flashlight activity from T6 (CB1, CB2, PB2) and PB1 flashlights involving T4, T6, & O2.

FIG. 11—QEEG correlates for non-clinical adolescents and adults (Group C) during delayed reading recall task In FIG. 11 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta2; PB2=Phase Beta2; RPD=Relative Power Delta; RPT=Relative Power Theta; RPA; Relative Power Alpha; RPB1=Relative Power Beta1; RPB2=Relative Power Beta2 MD=Magnivolts Delta; MT=Magnivolts Theta; MA=Magnivolts Alpha; MB1=Magnivolts Beta1; MB2=Magnivolts Beta2; PKFD=Peak Frequency Delta; PKFT=Peak Frequency Theta; PKFA=Peak Frequency Alpha; PKFB1=Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

Task Methodology—Auditory Memory

The auditory memory task involved the participant listening to 4 stories presented on a CD. They were instructed to close their eyes and listen to the story and try and memorize the story as it was presented (~50 seconds). The participants were then instructed to keep their eyes closed and recall the story to themselves (~40 seconds), and then open their eyes and tell the examiner what they recalled, at which point a memory score was obtained. Approximately 15-20 minutes later they were asked to close their eyes and recall the 4 stories that they heard. Following this task, the subjects were requested to tell the examiner what they recalled during the quiet recall period, and a delayed memory score was obtained.

FIG. 12 shows the QEEG correlates with auditory memory for Group A during the listening input condition. The figure shows SCC and phase involvement across the 0-32 Hz frequencies involving all locations and arousal variables involving relative power of beta1 and beta2 and PKAB1. QEEG variables negatively related to performance involve the lower frequencies (delta, theta) as well as MA, MB1, MB2, PKFB2.

FIG. 12—QEEG correlates for all (Group A) during auditory memory task—input condition In FIG. 12 the variables are defined as:
CD=Coherence Delta; CT=Coherence Theta; CA=Coherence Alpha; CB1=Coherence Beta1; PD=Phase Delta; PT=Phase Theta; PA=Phase Alpha; PB1=Phase Beta1; RPD=Relative Power Delta; RPT=Relative Power Theta; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFB2=Peak Frequency Beta2; PKAD=Peak Amplitude Delta; PKAB1=Peak Amplitude Beta1

FIG. 13 shows the QEEG correlations for Group B during the listening task for the non-clinical child group. The figure indicates significant positive involvement of RPA. RPB1, PKFA and fCPU (PA) and negative effects of all locations (RPD, RPT, PKAD), right hemisphere CB1 and PB1 activity and flashlight activity involving CB1 (T3, T4, T6), CB2 (T4), PB1 (T4, T6, O2, O1) and PB2 (T4, O2).

FIG. 13—QEEG correlates for children (Group B) during auditory memory task input condition In FIG. 13 the variables are defined as:
CB1=Coherence Beta1; CB2=Coherence Beta2PA=Phase Alpha; PB1=Phase Beta1; PB2=Phase Beta2; RPD=Relative Power Delta; RPT=Relative Power Theta; RPA=Relative Power Alpha; RPB1=Relative Power Beta1; PKFA=Peak Frequency Alpha; PKAD=Peak Amplitude Delta FIG. 14 shows the QEEG correlates with auditory memory for Group C during the input condition. The figure indicates all locations for PKFB1, central/posterior RPD, CPU (CA, PB1) and fCPU (CB2, PD, PA), left hemisphere PD and flashlight activity from T3 (CD), F7 (PD), T3 (PT) involvement in successful memory. The variables negatively related to performance involve frontal PKFB2, FPU (CB1, PB1), PPU (CA, CB1), right hemisphere CB1 and all lateral flashlight locations for CB1.

FIG. 14—QEEG correlates for adolescents and adults (Group C) during auditory memory task-input condition In FIG. 14 the variables are defined as:
CD=Coherence Delta; CA=Coherence Alpha; CB1=Coherence Beta1; CB2=Coherence Beta2; PD=Phase Delta; PT=Phase Theta; PA=Phase Alpha; PB1=Phase Beta1; RPD=Relative Power Delta; PKFB1=Peak Frequency Beta1; PKFB2=Peak Frequency Beta2

Figure 15:
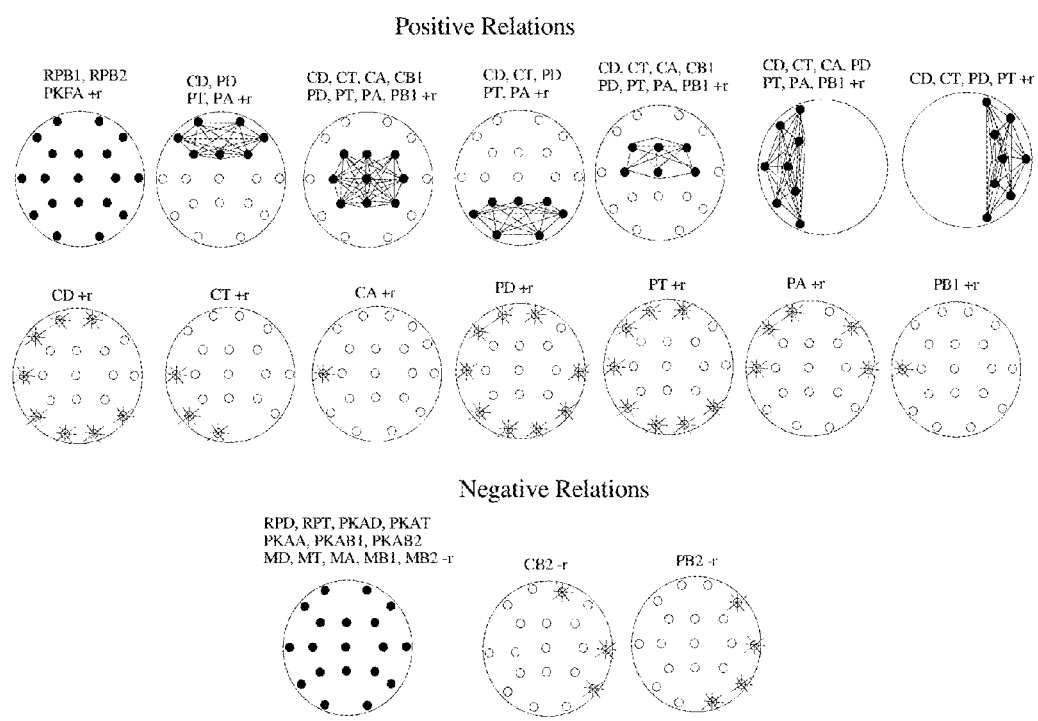
FIG. 15 presents QEEG correlates for all (Group A) during auditory immediate recall.

FIG. 15 shows the QEEG correlates with performance for Group A during the auditory immediate recall period. The figure shows diffuse involvement of SCC and phase relations (0-32 Hz), all locations for RPB1, RPB2 and PKFA and flashlight activity from all locations involving SCC relations (0-13 Hz) and phase relations (0-32 Hz). The QEEG variables negatively related to performance involve right hemisphere flashlight activity involving CB2 and PB2 and all locations for variables involving delta and theta as well as alpha (PKA, MA), beta1 (PKA, MB1) and beta2 (PKAB2, MB2).

FIG. 15—QEEG correlates for all (Group A) during auditory immediate recall

In FIG. 15 the variables are defined as:
CD=Coherence Delta; CT=Coherence Theta; CA=Coherence Alpha; CB=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFA=Peak Frequency Alpha; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

FIG. 16 shows the QEEG correlates with memory during the immediate recall task for Group B. The figure indicates all locations for RPA, RPB1, PKFA, central/posterior PKAB1 and FPU (PA) and fCPU (PA). The variable negatively related to performance involve all locations for RPD, RPT, PKAD, MD, PB2 (CPU, PPU, right hemisphere, right hemisphere flashlight activity) and frontal CT (Fp1, Fp2, F8).

FIG. 16—QEEG correlates for children (Group B) during auditory immediate recall

In FIG. 16 the variables are defined as:
CT=Coherence Theta; PB2=Phase Beta2; RPD=Relative Power Delta; RPT=Relative Power Theta; RPA=Relative Power Alpha; RPB1=Relative Power Beta1; MD=Magnivolts Delta; PKFA=Peak Frequency Alpha; PKAD=Peak Amplitude Delta; PKAB1=Peak Amplitude Beta1

Figure 17:
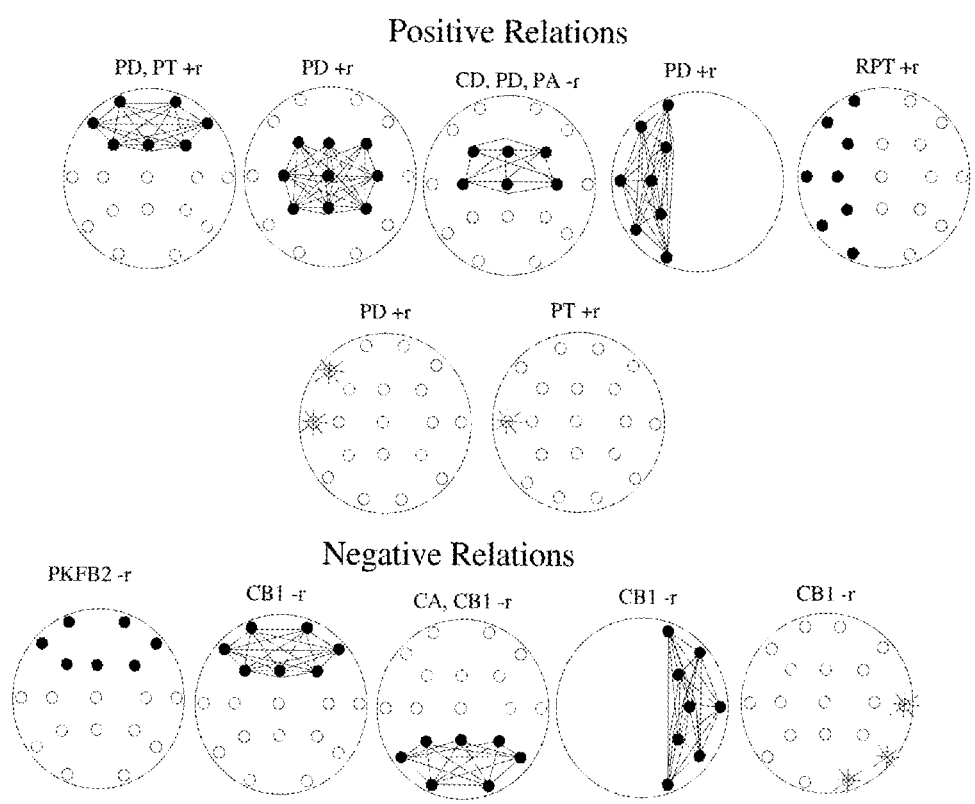
FIG. 17 presents QEEG correlates for adolescents and adults (Group C) during auditory immediate recall.

FIG. 17 shows the QEEG correlates for Group C during the auditory immediate recall task. The figure indicates FPU (PD, PT), CPU (PD), fCPU (CD, PA, PA), left hemisphere PD, left hemisphere RPT and flashlight activity from the left hemisphere (PD-F7, T3; PT-T3). The variables negatively related to performance involve frontal PKFB2, FPU (CB1), PPU (CA, CB1), right hemisphere CB1 and flashlight activity involving CB1 in right hemisphere posterior locations.

FIG. 17—QEEG correlates for adolescents and adults (Group C) during auditory immediate recall In FIG. 17 the variables are defined as:
CD=Coherence Delta; CA=Coherence Alpha; CB1=Coherence Beta1; PD=Phase Delta; PT=Phase Theta; PA=Phase Alpha; RPT=Relative Power Theta; PKFB2=Peak Frequency Beta2

FIG. 18 shows the QEEG correlates of delayed auditory recall for all participants (Group A). The figure indicates that the positive correlates involve diffuse SCC and phase relations involving 0-32 Hz, a left hemisphere dominant pattern involving CA, CB1, PA, & PB1, and diffuse flashlight activity involving the 0-32 Hz frequencies (mostly phase relations). The QEEG variables negatively related to performance include the lower frequencies (0-8 Hz), magnitude and peak amplitude values for all the frequencies as well as the flashlight activity (CB2) from T4.

FIG. 18—QEEG correlates for all participants (Group A) during delayed auditory memory recall task In FIG. 18 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPA; Relative Power Alpha; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFD=Peak Frequency Delta; PKFT=Peak Frequency Theta;

PKFA=Peak Frequency Alpha; PKFB1=Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

FIG. 19 shows the QEEG correlates of delayed recall for the non-clinical children's group (B). The QEEG variables which were positively related to performance involve all locations for PKFA, FPU (CD), CPU (CD, PD, PA) and left hemisphere RPB1. Variables negatively related to performance involve all locations for RPT, PKAT, MT, right frontal RPD and a negative flashlight activity from T4 (CB1).

FIG. 19—QEEG correlates for non-clinical children (Group B) during delayed auditory memory recall task In FIG. 19 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPA; Relative Power Alpha; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFD=Peak Frequency Delta; PKFT=Peak Frequency Theta; PKFA=Peak Frequency Alpha; PKFB1=Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

FIG. 20 shows the QEEG correlates of delayed auditory recall for non-clinical adolescents and adults (Group C). The figure shows the positive QEEG correlates involve CPU (CB2, PB1), frontal CPU (CB2, PA) and flashlight activity from f7 (CD, PB1). Flashlight activity from T4 (CB2, PB2) were a negative influence on performance.

FIG. 20—QEEG correlates for non-clinical adolescents & adults (Group C) during delayed auditory memory recall task In FIG. 20 the variables are defined as:
CD=Coherence Delta; CT=Coherence Theta; CA=Coherence Alpha; CB1=Coherence Beta1; CB2=Coherence Beta2; PD=Phase Delta; PT=Phase Theta; PA=Phase Alpha; PB1=Phase Beta1; PB2=Phase Beta2; RPD=Relative Power Delta; RPT=Relative Power Theta; RPA; Relative Power Alpha; RPB1=Relative Power Beta1; RPB2=Relative Power Beta2; MD=Magnivolts Delta; MT=Magnivolts Theta; MA=Magnivolts Alpha; MB1=Magnivolts Beta1; MB2=Magnivolts Beta2; PKFD=Peak Frequency Delta; PKFT=Peak Frequency Theta; PKFA=Peak Frequency Alpha; PKFB1=Peak Frequency Beta1; PKFB2=Peak Frequency Beta2; PKAD=Peak Amplitude Delta; PKAT=Peak Amplitude Theta; PKAA=Peak Amplitude Alpha; PKAB1=Peak Amplitude Beta1; PKAB2=Peak Amplitude Beta2

Task Methodology—Problem Solving/Ravens Matrices

Eleven items from the Ravens matrices were employed (D & E series). The participants were instructed on the nature of the problems with a warm up example. The score was based upon whether they obtained a correct response on the first guess. Due to the high number of artifacts resulting from the task, the goal was to obtain 400-500 epochs of data.

FIG. 21 shows the QEEG correlates with performance for Group C (non-clinical adolescents and adults). The figure indicates FPU (CA), left hemisphere CA, flashlight activity from F7 (CA, PA, PB1, PB2), F8 (CB1) and CA (F8, T3, T6) involvement in successful performance. Additionally, all locations for the variables of PKAD, PKAA, PKT, MD, & MA, right frontal RPA, left posterior MT and PKAT and right posterior RPB2, PKAB2 and PKFB1 were determinants of successful performance. The QEEG variable which as negatively associated with performance involve all locations for PKFA.

FIG. 21—QEEG correlates for adolescents and adults (Group C) during Ravens Progressive Matrices In FIG. 21 the variables are defined as:
CA=Coherence Alpha; CB1=Coherence Beta1; PA=Phase Alpha; PB1=Phase Beta1; PB2=Phase Beta2; RPB2=Relative Power Beta2; MD=Magnivolts Delta; MT=Magnivolts Theta; MA=Magnivolts Alpha; PKFT=Peak Frequency Theta; PKFA=Peak Frequency Alpha; PKFB1=Peak Frequency Beta1; PKAD=Peak Amplitude Delta; PKAA=Peak Amplitude Alpha; PKAB2=Peak Amplitude Beta2

FIG. 22 shows the QEEG correlates for Group B (non-clinical children) and performance. The sole variable positively related to performance was central/posterior RPB1. The variables negatively related to performance involve all locations for PKAT, central/posterior locations for RPT, MT, left frontal MT, CPU (CT), and F7 (PT).

FIG. 22—QEEG correlates for children (Group B) during Ravens Progressive Matrices In FIG. 22 the variables are defined as:
CT-Coherence Theta; PT-Phase Theta; RPT-Relative Power Theta; RPB1=Relative Power Beta1; MT=Magnivolts Theta; PKFD=Peak Frequency Delta; PKFT=Peak Frequency Theta; PKAT=Peak Amplitude Theta

The invention claimed is:

1. A method for improving reading memory by engaging a subject in a combined cognitive and electrophysiological assessment of how a mind responds to a reading task to ascertain a subject's values on the negative and positive quantitative EEG (QEEG) variables of reading memory while a subject performs each of the following tasks: reading input, immediate recall and delayed recall, the method comprising the steps of:

exposing the subject to each respective task;

attaching an electro-cap on a subject's head;

measuring QEEG brain variables in 19 locations comprising of coherence, phase, relative power, peak frequency, peak amplitudes, magnitudes at 5 frequency bands comprised of 0-4 Hz, 4-8 Hz, 8-13 Hz, 13-32 Hz, & 32-64 Hz during each respective task;

recording the QEEG measurements and memory measures (subject's verbal recall of material);

converting the subject's QEEG data obtained during the recording into an ASCII file and creating a spreadsheet of the average values of each of the variables during each of the respective specific tasks;

importing the QEEG data, represented in the spreadsheet, into a statistical computer analysis program loaded on a computer, examining the subjects QEEG data during the reading input task with the QEEG correlates of performance in one of the following relevant databases that the subject is a member of group A) all participants, B) non-clinical children, or C) non-clinical adolescents and adults; the subject's data is analyzed for deviation from the average values on the variables which are linearly related (positively and negatively) to performance in the relevant database;

analyzing at least the subject's phase and coherence variables in at least the 13-32 & 32-64 Hz bands for deviation from the average values of the 19 QEEG variables which are linearly related (positively and negatively) to performance in the relevant database;

determining if the subject's positively related variables for at least phase and coherence in at least the 13-32 & 32-64 Hz bands are below the average in the relevant database;

for the positively related variables that are below the below the average value, employing EEG biofeedback protocols, using a biofeedback device, to increase the value of one or more of the positively related QEEG variables, until the value of the one or more QEEG variables, in subsequent EEG measurement and data processing, is at the average value or above, in the relevant database, thereby improving the subject's reading memory;

determining if the subject's negatively related variables for at least phase and coherence in the at least 13-32 & 32-64 Hz bands are above the average in the relevant database; and for the negatively related variables that are above the average value, employing EEG biofeedback protocols, using a biofeedback device, to decrease the value of one or more of the negatively related QEEG variables, until the value of the one or more QEEG variables in subsequent EEG measurement and data processing, is at the average value or below, in the relevant database, thereby improving the subject's reading memory.

2. A method for improving auditory memory by engaging a subject in a combined cognitive and electrophysiological assessment of how a mind responds to an auditory memory task to ascertain a subject's values on the negative and positive quantitative EEG (QEEG) correlates of auditory memory while a subject performs each of the following tasks: auditory input, immediate recall and delayed recall, the method comprising the steps of:

exposing the subject to each respective task;
attaching an electro-cap on a subject's head;
measuring QEEG brain variables in 19 locations comprising of coherence, phase, relative power, peak frequency, peak amplitudes, magnitudes at 5 frequency bands comprised of 0-4 Hz, 4-8 Hz, 8-13 Hz, 13-32 Hz, & 32-64 Hz during each respective task;
recording the QEEG measurements and memory measures (subject's verbal recall of material);
converting the subject's QEEG data obtained during the recording into an ASCII file and creating a spreadsheet of the average values of each of the variables during each of the respective specific tasks;
importing the QEEG data, represented in the spreadsheet, into a statistical computer analysis program loaded on a computer;
examining the subject's QEEG data during the auditory input task with the QEEG correlates of performance in one of the following relevant databases that the subject is a member of group A) all participants, B) non-clinical children, or C) non-clinical adolescents and adults; the subject's data is analyzed for deviation from the average values on the variables which are linearly related (positively and negatively) to performance in the relevant database;

analyzing at least the subject's phase and coherence variables in at least the 13-32 & 32-64 Hz bands for deviation from the average values of the 19 QEEG variables which are linearly related (positively and negatively) to performance in the relevant database;

determining if the subject's positively related variables at least for phase and coherence in at least the 13-32 & 32-64 Hz bands are below the average in the relevant database;

for the positively related variables that are below the below the average value, employing EEG biofeedback protocols, using a biofeedback device, to increase the value of one or more of the positively related QEEG variables, until the value of the one or more QEEG variables, in subsequent EEG measurement and data processing, is at the average value or above, in the relevant database, thereby improving the subject's auditory memory;

determining if the subject's negatively related variables for at least phase and coherence in at least the 13-32 & 32-64 Hz bands are above the average in the relevant database; and for the negatively related variables that are above the average value, employing EEG biofeedback protocols, using a biofeedback device, to decrease the value of one or more of the negatively related QEEG variables, until the value of the one or more QEEG variables in subsequent EEG measurement and data processing, is at the average value or below, in the relevant database, thereby improving the subject's auditory memory.

3. A method for improving problem solving ability by engaging a subject in a combined cognitive and electrophysiological assessment of how a mind responds to a problem solving task (Raven's matrices or similar measures) to ascertain a subject's values on the negative and positive quantitative EEG (QEEG) correlates of problem solving during the task, the method comprising the steps of:

exposing the subject to a problem solving task;
attaching an electro-cap on a subject's head;
measuring QEEG brain variables in 19 locations comprising of coherence, phase, relative power, peak frequency, peak amplitudes, magnitudes at 5 frequency bands comprised of 0-4 Hz, 4-8 Hz, 8-13 Hz, 13-32 Hz, & 32-64 Hz during the task;
recording the QEEG measurements and problem solving measures;
converting the subject's QEEG data obtained during the recording into an ASCII file and creating a spreadsheet of the average values of each of the variables during each of the respective specific tasks;
importing the QEEG data, represented in the spreadsheet, into a statistical computer analysis program loaded on a computer;
examining the subject's QEEG data during the problem solving task with the QEEG correlates of performance in one of the following relevant databases that the subject is a member of group A) all participants, B) non-clinical children, or C) non-clinical adolescents and adults; the subject's data is analyzed for deviation from the average values on the variables which are linearly related (positively and negatively) to performance in the relevant database;

analyzing at least the subject's phase and coherence variables in at least the 13-32 & 32-64 Hz bands for deviation from the average values of the 19 QEEG variables which are linearly related (positively and negatively) to performance (on problem solving measures) in the relevant database;

determining if the subject's positively related variables for at least phase and coherence in at least the 13-32 & 32-64 Hz bands are below the average in the relevant database;

for the positively related variables that are below the below the average value, employing EEG biofeedback protocols, using a biofeedback device, to increase the value of one or more of the positively related QEEG variables, until the value of the one or more QEEG variables, in subsequent EEG measurement and data processing, is at the average value or above, in the relevant database, thereby improving the subject's problem solving ability;

determining if the subject's negatively related variables for at least phase and coherence in at least the 13-32 & 32-64 Hz bands are above the average in the relevant database; and for the negatively related variables that are above the average value, employing EEG biofeedback protocols, using a biofeedback device, to decrease the value of one or more of the negatively related QEEG variables, until the value of the one or more QEEG variables in subsequent EEG measurement and data processing, is at the average value or below, in the relevant database, thereby improving the subject's problem solving ability.

* * * * *